United States Patent [19]

Ganfield et al.

[11] 4,438,030

[45] Mar. 20, 1984

[54] ANTIBODIES TO IMMUNOGENIC PEPTIDES AND THEIR USE TO PURIFY HUMAN FIBROBLAST INTERFERON

[75] Inventors: David J. Ganfield, Clementon, N.J.; Michael W. Hunkapiller, San Gabriel, Calif.; Ernest Knight, Jr.; Bruce D. Korant, both of Wilmington, Del.

[73] Assignee: E. I. Du Pont de Nemours and Company, Wilmington, Del.

[21] Appl. No.: 363,743

[22] Filed: Mar. 30, 1982

Related U.S. Application Data

[62] Division of Ser. No. 172,466, Jul. 25, 1980, Pat. No. 4,341,761.

[51] Int. Cl.³ .................... C07C 103/52; A61K 45/02
[52] U.S. Cl. .................... 260/112.5 R; 260/112 R; 424/85; 436/536; 436/547
[58] Field of Search ...... 424/85; 260/112 R, 112.5 R; 436/536, 547

[56] References Cited

U.S. PATENT DOCUMENTS

3,725,545  4/1973  Maes .................................. 424/180
4,213,964  7/1980  Buckler .............................. 424/85

OTHER PUBLICATIONS

Phassi, Immunochemistry of Proteins, vol. 2, pp. 1–3, Plenum Press, 1977.
Cuatrecasas et al., Proc. Nat. Acad. Sci., vol. 61, pp. 636–643, 1968.
"Affinity Chromatography", Pharmacia Fine Chemicals AB, 1979, pp. 92–95.
Carraway, in "Methods of Radioimmunoassay", Jaffe and Behrman, editors, 2nd Edition, N.Y., 1979, pp. 143 to 149.
Ruddon et al., in J. Biol. Chem., 255, 1000 to 1007 (1980).
Arnon et al., in Proc. Nat. Acad. Sci., USA, 68, 1450 to 1455 (1971).
Anfinsen et al., Proc. Nat. Acad. Sci., USA, 71, 3139 to 3142 (1974).
Paucker et al., in "Effects of Interferon On Cells, Viruses and the Immune System", edited by Geraldes, Academic Press, NY, 1975, 639 to 651.
Chudzio, J. Immunol. Methods, 1976, 13(1), 63 to 69 [Chem. Abs. 86, 41609Z (1977)].
Gresser et al., J. Exp. Med., 144, 1305 to 1315 (1976).
Skurkovich et al., J. Immunol. Methods, 1978, 19 (2,3), 119 to 124, [Chem. Abs, 88, 134627k (1978)].
Paucker, Tex. Rep. Biol. Med., 1977, 35, 23 to 28.
Berg et al., Scand. J. Immunol., 8, 429 to 436 (1978).
Dalton et al., Infection and Immunity, 19, 570 to 574 (1978).
Stewart, in "Interferons And Their Actions", Gottlieb, editor, CRC Press, N.Y., 1977, pp. 49 to 72.
Houghton et al., in Nucl. Acids Res., 8, pp. 1913 to 1931, 2885 to 2894 (1980).
Houghton, in Nature, 285, 536 (1980).
Derynck et al., in Nature, 285, 542 to 547 (1980).
Taniguchi et al. in Gene, 10, 11 to 15 (1980).
Taniguchi et al., in Nature, 285, 547 to 549 (1980).
Knight et al., in Science, 207, 525 (1980).
Shimizu et al., Biochem. Biophys. Res. Communications 103, pp. 1149 to 1156 (1981).

*Primary Examiner*—Blondel Hazel
*Attorney, Agent, or Firm*—James A. Costello

[57] ABSTRACT

Antibodies to the twenty-one acid peptide: (X-Ser-Tyr-Asn-Leu-Leu-Gly-Phe-Leu-Gln-Arg-Ser-Ser-Asn-Phe-Gln-Y-Gln-Lys-Leu-Leu)$_n$, where X is Met or Ser, Y is His or Cys and n is 1 to 12; peptide/protein conjugates and antibodies thereto; process for producing the antibodies; and processes for assaying human fibroblast interferon and for purifying it.

2 Claims, No Drawings

ANTIBODIES TO IMMUNOGENIC PEPTIDES AND THEIR USE TO PURIFY HUMAN FIBROBLAST INTERFERON

CROSS-REFERENCE TO RELATED APPLICATION

This is a divisional application of copending application Ser. No. 172,466, filed on July 25, 1980, now U.S. Pat. No. 4,341,761.

BACKGROUND OF THE INVENTION

1. Field of the Invention

This invention concerns antibodies to particular immunogenic peptides and peptide conjugates and to processes for making the antibodies and using them to assay and purify human fibroblast interferon (HFIF).

2. State of the Art

It is known generally that peptides can be used to produce antibodies which are complexed with proteins in an assay for or purification of the protein: Carraway, "Methods of Radio-immunoassay", Jaffe and Behrman, editors, 2nd Edition, N.Y., 1979, pages 143 to 149. Rudden et al, in J. Biol. Chem., 255, 1000 to 1007 (1980), described the use of antiserum to a synthetic polypeptide representing the 15 carboxyl-terminal amino acids of the human chorionic gonadotropin (hCG) hormone β subunit for precipitation of hCG-β subunit. In another study, Arnon et al, Proc. Nat. Acad. Sci., USA, 68, 1450 to 1455 (1971), used a polymer conjugate of a synthetic peptide consisting of a slightly modified amino acid sequence of residues 64 to 82 of lysozyme, to produce antibodies to lysozyme in rabbits and goats.

Interferons are protein antiviral agents which can be assayed and purified by reaction with specific antibodies. However, until now it was necessay to employ interferon itself to induce antibody formation. The difficulty of obtaining interferon has caused attendant difficulties in its assay and purification. The following references concern interferon assay and purification:

(1) Anfinsen et al, Proc. Nat. Acad. Sci. USA, 71, 3139 to 3142 (1974), describe partial purification of human leukocyte interferon by affinity chromatography using antibodies;

(2) Paucker et al in "Effects of Interferon On Cells, Viruses and the Immune System", edited by Geraldes, Academic Press, New York, 1975, 639 to 651, describe the purification of mouse interferon by antibody affinity chromatography;

(3) Chudzio, J. Immunol. Methods, 1976, 13(1), 63 to 69 (Chem. Abs., 86, 41609Z (1977)), describes a bioassay employing polyethylene glycol for measuring the level of interferon neutralizing antibodies;

(4) Gresser et al, J. Exp. Med., 144, 1305 to 1315 (1976), describe the use of highly potent sheep antimouse interferon serum to demonstrate the importance of interferon in the early response to some viral infections;

(5) Skurkovich et al, J. Immunol. Methods, 1978, 19 (2,3), 119 to 124 (Chem. Abs., 88, 134627k (1978)) studied quantitative determination of human leukocyte interferon by microfluorometric immunoassay with fluorescein isothiocyanate-labeled antibodies;

(6) Paucker, Tex. Rep. Biol. Med., 1977, 35, 23 to 28, reviewed antigenic properties of interferon proteins;

(7) Berg et al, Scand. J. Immunol., 8, 429 to 436 (1978), studied purification of human leukocyte, fibroblast and lymphoblastoid interferons by use of antibodies bound to sepharose columns;

(8) Dalton et al, Infection and Immunity, 19, 570 to 574 (1978), studied production of antibodies to human interferon in mice using highly purified human leukocyte interferon for antibody production; and (9) Stewart, in "Interferons And Their Actions", Gottlieb, editor, CRC Press, N.Y., 1977, pages 49 to 72, summarizes several methods for purifying and characterizing interferons.

The following references concern interferon itself. Knight et al, in Science, 207, 525 (1980) described a sequence of 13 amino-terminal residues of homogeneous human fibroblast interferon. Houghton et al, Nucl. Acids Res., 8, pages 1913 to 1931 (1980), disclosed the sequence of 47 amino-terminal residues of human fibroblast interferon. Additional references are: Houghton, Nature, 285, 536 (1980); Derynck et al., ibid., 542 to 547 (1980); Taniguchi et al., ibid., 547 to 549 (1980); and Taniguchi et al., Gene, 10, 11 to 15 (1980).

Although it is known generally that peptides and peptide/protein conjugates can produce antibodies, there is nothing to suggest the particular peptide of this invention, or that said peptide will produce antibodies which react with human fibroblast interferon. In fact, there appears to be no teaching in the art concerning production of interferon antibodies by any peptide or protein other than interferon itself.

The subject matter of this invention is related to that of U.S. Pat. No. 4,311,639.

SUMMARY OF THE INVENTION

This invention concerns antibodies to human fibroblast interferon produced in response to immunogenic peptides comprising the following amino acid sequence:

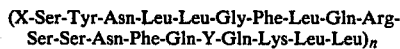

wherein:
- X is selected from Met and Ser,
- Y is selected from His and Cys,
- n is 1 to 12. This invention also concerns antibodies produced in response to peptide/protein conjugates which are themselves an element of this invention. Preferred proteins are rabbit albumin and ovalbumin. All of the antibodies of this invention are characterized by reacting specifically with the peptides and peptide/protein conjugates as well as with human fibroblast interferon.

This invention also concerns a process for producing antibodies, comprising the step of introducing the described 21 amino acid peptide(s) into an animal medium capable of producing antibodies in response to human fibroblast interferon (HFIF), the antibodies produced in response to said peptide characterized by being antibodies to HFIF.

This invention also concerns a process for assaying HFIF in a mixture of proteins. For example, the protein mixture is contacted with antibodies produced in response to one or more of the designated 21 amino acid peptides, said antibodies first being attached to a solid phase such as a polymer, e.g., agarose, poly(vinyl chloride), etc., or bacteria. An interferon-antibody complex is formed, and interferon is separated from the liquid phase. In another technique, interferon is allowed to react with the antibodies in solution. The interferon-antibody complex formed is then separated by reaction with another antibody, with *Staphylococcus aureus* or with Protein A coupled to agarose. Analysis of the separated complex for interferon can be accomplished, for example by admixture of radiolabeled or enzyme-labeled interferon using well-known procedures.

This invention also concerns the process for purifying HFIF comprising the additional step(s) of separating the interferon-antibody complex from the other protein(s) and separating the HFIF from the antibody. Purification of HFIF can be carried out using antibody affinity chromatography employing antibodies produced by the peptides of this invention. In a typical procedure, antibodies are attached to a polymeric support, e.g., agarose, in the form of a column. Solutions containing HFIF are passed over the column, and interferon is adsorbed by the antibodies. Subsequently, purified interferon is eluted from the column using acidic buffers, salt gradients, or other known techniques. Example 8 demonstrates the use of an immunoabsorbent column in affinity chromatography.

In a similar manner, the antibodies of the invention cann be employed to purify protein and protein fragments of HFIF containing one or more of the designated peptide sequences. In this regard, description of the purification of HFIF includes, as well, the concept of purifying protein and protein fragments of HFIF which contain one or more of the designated peptide sequences.

By "immunogenic" is meant that the peptides of this invention induce antibodies when injected into animals without the necessity of coupling the peptides to carrier-proteins. Nevertheless, the peptides may be coupled to carrier-proteins if it is desired to do so, said coupling having no effect on the characteristic immunogenic nature of the peptide.

DETAILS OF THE INVENTION

In this application, the following shorthand expressions (wherein n=1) are used for simplicity:

| Peptide | Where |
|---------|-------|
| 1a | X = Met, Y = His |
| 1b | X = Ser, Y = His |
| 1c | X = Met, Y = Cys |
| 1d | X = Ser, Y = Cys. |

All chiral amino acid residues identified herein are in the natural or L-configuration. In keeping with standard peptide nomenclature, abbreviations for chiral amino acid residues are as follows:

| Arg | L-arginine | Leu | L-leucine |
|-----|-----------|-----|-----------|
| Asn | L-asparagine | Lys | L-lysine |
| Cys | L-cysteine | Met | L-methionine |
| Gln | L-glutamine | Phe | L-phenylalanine |
| Gly | glycine | Ser | L-serine, and |
| His | L-histidine | Tyr | L-tyrosine. |

General Procedure For Making The Peptides

Solid-phase peptide synthesis is employed. Representative N-terminus protecting groups which can be employed include acyl-type protecting groups, aromatic urethane-type protecting groups, alkyl-type protecting groups, trialkylsilane groups, or aliphatic urethane protecting groups. The term "acyl-type protecting groups" refers to groups illustrated by but not restricted to formyl, trifluoroacetyl, tosyl, nitrosulfonyl, and the like.

The term "aromatic urethane-type protecting groups" includes groups such as benzyloxycarbonyl, p-methoxybenzyloxycarbonyl, p-biphenylisopropyloxycarbonyl, 2,5-dimethoxyphenylisopropyloxycarbonyl, and the like. The term "cycloalkyl urethane protecting groups" includes groups such as cyclopentyloxycarbonyl, adamantyloxycarbonyl, cyclohexyloxycarbonyl, isobornyloxycarbonyl, and the like. "Alkyl-type protecting groups" are those commonly used in the art such as the trityl group. "Trialkylsilane groups" includes trimethylsilane, triethylsilane, tributylsilane, and the like.

The preferred protecting groups, the "aliphatic urethane-protecting groups", include tert-butyloxycarbonyl, diisopropyloxycarbonyl, isopropyloxycarbonyl, allyloxycarbonyl, and the like.

In selecting a particular side-chain protecting group to be used, several conditions must be met: (a) the protecting group must be stable to the reagent under reaction conditions selected for removing the α-amino protecting group at each step of the synthesis; (b) the protecting group must retain its protecting properties and not be chemically modified; and (c) the side-chain protecting group must be removable at the end of the solid-phase synthesis under reaction conditions that will not alter the peptide chain.

Examples of suitable side-chain protecting groups include protecting groups for the phenolic hydroxyl group of tyrosine including tetrahydropyranyl, tert-butyl, trityl, benzyl, 2,4-dichlorobenzyl, benzyl-oxycarbonyl, O-benzyl ether, or 4-bromobenzyloxycarbonyl (4-BrZ); protecting groups for the alcohol hydroxy functions of serine including the groups suitable for protection of phenolic hydroxyl groups; protecting groups for the epsilon amino group of lysine including trifluoroacetyl, benzyloxycarbonyl or, preferably, 2-chlorobenzyloxycarbonyl; protecting groups for the guanidine group of arginine including nitro or N-tosyl; protecting groups for the imidazolyl group of histidine including N-tosyl and protecting groups for the thio group of cysteine, such as p-methoxybenzyl.

The polystyrene resin support is preferably a copolymer of styrene with about 1 to 2 weight percent of divinylbenzene as a cross-linking agent which causes the polystyrene polymer to be completely insoluble in most organic solvents.

Peptide synthesis is commenced from the C-terminal end of the peptide using an α-amino-protected resin. A suitable starting material can be prepared, for instance, by attaching the required α-amino acid to a chloromethylated resin, a hydroxymethyl resin, or a benzhydrylamine resin. One such chloromethylated resin is sold under the trade name BIO-BEADS SX-1 by Bio-Rad Laboratories, Richmond, Calif., and the preparation of the hydroxymethyl resin is described by Bodanszky et al, Chem. & Ind., London, 1597 (1966). The benzhydrylamine resin has been described by Pietta and Marshall, Chem. Commun., 650 (1970) and is commercially available from Beckman Instruments, Palo Alto, Calif.

An α-amino protected amino acid can be coupled to the chloromethylated resin by reaction with the cesium salt using cesium carbonate or cesium bicarbonate, according to the method described by Gisin, Helv. Chim. Acta., 56, 1476 (1973). After the initial coupling, the α-amino protecting group is removed by a choice of reagents including trifluoroacetic acid or hydrochloric acid solution in organic solvents at room temperature. After removal of the α-amino protecting group, the remaining protected amino acids are coupled stepwise in the desired order to obtain the desired peptide sequence. Each protected amino acid can be reacted in a 3-fold excess using an appropriate carboxyl group activator such as dicyclohexylcarbodiimide in solution in, for example, methylene chloridedimethylformamide mixtures.

After the amino acid sequence has been completed, the peptide is removed from the resin support by treating with a reagent such as hydrogen fluoride which not only cleaves the peptide from the resin, but also cleaves all remaining side-chain protecting groups. When the chloromethylated resin is used, hydrogen fluoride treatment results in the formation of the free peptide acids. When the benzhydrylamine resin is used, hydrogen fluoride treatment results directly in the free peptide amines.

Alternatively, when the chloromethylated resin is employed, the side-chain protected peptide can be cleaved by treatment of the peptide-resin with ammonia to give the desired side-chain protected amide or with an alkylamine to give a side-chain protected alkylamide or dialkylamide. Side-chain protection is then removed in the usual fashion by treatment with hydrogen fluoride to give the free amides, alkylamides, or dialkylamides.

Antibody Production

Several methods are known for preparing antibodies to synthetic peptides. A description of such a method can be found in Williams et al, Methods In Immunology and Immunochemistry, Academic Press, New York and London, 1967, and in the Handbook of Experimental Immunology, 3rd edition, Weir, editor, Blackwell Scientific Publications, Oxford & London, 1978, especially the first chapter by Sela et al.

The particular manner in which a peptide of this invention can be bonded to a carrier-protein (if it is desired to do so) will depend on the functionalities which are available on the peptide and the carrier, the number of peptide groups to be conjugated, and the like. Groups which find use include amino groups; or carboxy groups which can be activated by employing the mixed carbonic acid anhydride or carbodiimide; imidates; diazo groups; alpha-haloketones; and the like.

Peptides or peptide-protein conjugates can be injected in the fluid state; adsorbed to insoluble particles, such as alumina; or incorporated in matrix materials such as agar, calcium alginate, or Freund's adjuvants ("complete" or "incomplete"). Other adjuvants include polyacrylamide gel, bentonite, and proteins such as methylated bovine serum albumin. Complete Freund's adjuvant, a suspension of mycobacteria in oil, is given with an aqueous preparation of the immunogen in the form of an emulsion stabilized with lanolin, lanolin derivatives, e.g., Aquaphor, mannide mono-oleate or Arlacel A. The complete adjuvant is distinguished from the incomplete adjuvant, by having mycobacteria, e.g., M. butyricum or M. tuberculosis.

Immunization can be carried out in a variety of ways with a number of different animals such as horses, cows, pigs, dogs, sheep, goats, rodents, rabbits, or hares. The peptides or peptide/protein conjugates can be injected interperitoneally, intramuscularly, subcutaneously, and the like. When employing Freund's adjuvants, usually in combination with saline, the amount of immunogen employed will vary depending on the particular immunogenic material and the number and period of prior injections. Usually, about 0.1 to 5 mg of immunogenic material will be employed per ml of solution. The total amount of immunogenic material and solution will depend on the size, nature and weight of the animal. The initial injection will normally be at a number of sites, aliquots of the composition being employed.

After the first injections of immunogen, a period of time is allowed to pass before booster injections are introduced, normally two to five weeks. The animals may be bled and the serum assayed so as to follow the formation of the desired antibody. The animals will usually be bled about one week after an injection. Collected blood is allowed to clot and the serum containing the antibodies is drawn off after centrifugation.

The serum can be treated in various ways, depending on its subsequent use. It can be fractionated by employing ethanol, neutral salts such as ammonium sulfate, sodium sulfate, or the like. Alternatively, the serum can be chromatographed on various modified cellulose columns, e.g., diethylaminoethylcellulose or carboxymethylcellulose; or, various physical means can be employed to purify and/or isolate the desired antibodies.

The antibodies are primarily $\gamma$-globulins with a molecular weight of about 150,000. Variations of the antibody structures will give different binding constants. Preservatives can be employed to stabilize the antibodies and the antibodies will normally be stored at reduced temperatures.

General Procedure For Radiolabeling

Human fibroblast interferon was radioiodinated by a modification of the procedure of Hunter and Greenwood, Nature (London) 195, 495 to 496 (1962). First, 500 ng of interferon in 20 $\mu$l of 0.15 M sodium chloride/0.05 M sodium phosphate, pH 7.2, was reacted at 0° with 1 mCi of $^{125}$I ($2 \times 10^6$ mCi/matom) and 10 $\mu$l of a 0.2 mg/ml aqueous solution of chloramine-T (prepared immediately before use). After 5 minutes, 5 $\mu$l of a 0.4 mg/ml aqueous solution of sodium metabisulfite was added to stop the reaction. Then, 10 $\mu$l of a mixture containing 25% glycerol, 5 mM of dithiothreitol, 1 mg/ml of bovine serum albumin, and 5 mM of potassium iodide in phosphate-buffered saline was added. The products were passed through a 0.6 cm (ID) $\times$ 10 cm column of polyacrylamide gel filtration resin (Bio-Gel ®) equilibrated with 1 mg/ml of bovine serum albumin in phosphate-buffered saline to separate the labeled interferon (in the "void" volume) from unreacted $^{125}$I-iodide. The specific activity of the product was estimated to be approximately 20 $\mu$Ci/$\mu$g. Radiolabeling of the peptide sequences with $^{125}$I was carried out using essentially the same procedure to obtain $^{125}$I-labeled peptide.

The following Preparations describe the making of the peptides employed to induce the antibodies of this invention for use in the processes of this invention. The Examples, illustrating the subject matter of this invention, follow the Preparations. In both Preparations and Examples, part and percentages are by weight and degrees are Celsius unless otherwise stated. Peptides 1a, 1b, 1c and 1d are fully defined above.

PREPARATION A

Preparation of Peptide Sequence 1a (Wherein X is Met and Y is His)

Peptide 1a is made in accordance with the General Procedure outlined above, under the heading "Details of the Invention", with the following additional details. A t-butyloxycarbonyl (t-Boc)-Leu hydroxymethyl resin was prepared by reaction of t-Boc-Leu, hydroxymethylpolystyrene resin, dicyclohexylcarbodiimide and pyridine in a molar ratio of 2/1/2/2. Alternatively, the resin can be prepared by reaction of the cesium salt of t-Boc-Leu with chloromethylpolystyrene resin. Subsequent reaction of the resin with the necessary sequence of amino acids to obtain the desired Peptide 1a used in each case the t-Boc protecting group for the $N^\alpha$-nitrogen, and total protection of all other reactive groups. The following protecting groups were employed:

| Amino Acid | Protecting Group |
|---|---|
| Lys | 2-chlorobenzyloxycarbonyl |
| His | N—tosyl |
| Ser | O—benzyl ether |
| Arg | N—tosyl |
| Tyr | 4-bromobenzyloxycarbonyl |

The amino acid sequence was built up in the following order. Leucine was first attached to the resin. Next another leucine was attached to the first residue followed in turn by lysine, glutamine, histidine, glutamine, phenylalanine, asparagine, serine, serine, arginine, glutamine, leucine, phenylalanine, glycine, leucine, leucine, asparagine, tyrosine, serine, and finally methionine.

The blocked peptide was removed from the resin with hydrogen fluoride in the usual manner. The product was desalted by passing it through a polyacrylamide gel filtration resin (Bio-Gel ® P6 resin, a product of Bio-Rad Laboratories) using 1 N acetic acid solvent, and the effluent was lyophilized. This crude peptide product was further purified by counter-current distribution using a mixture of 1-butanol/acetic acid/water, and the peptide was isolated from the lower aqueous phase.

Peptide 1a was characterized by high pressure liquid chromatography (HPLC) using UV detection at 210 and 275 nm, thin layer chromatography, and electrophoresis. The data indicated a high degree of purity; for example, HPLC indicated >98% purity. Peptide analysis obtained from amino acid analyses suggested a purity of about 86%. The peptide was soluble in water, 1:1 tetrahydrofuran/water, and 1:1 acetonitrile/water. It was insoluble in tetrahydrofuran and acetonitrile, and it was swollen by methanol.

PREPARATION B

Preparation of Peptide Sequence 1b (Wherein X is Ser and Y is His)

Peptide 1b is made by the General Procedure described above under "Details of the Invention". Additional process description is as follows.

The peptide was prepared by solid-phase peptide synthesis using a commercially available t-Boc-Leu resin, 0.65 meq/g. Reaction of the resin with the necessary sequence of amino acids to obtain Peptide 1b used in each case the t-Boc protecting group for the $N^\alpha$-nitrogen, and total protection of all other reactive groups. The protecting groups employed were:

| Amino Acid | Protecting Group |
|---|---|
| Lys | benzyloxycarbonyl (ε-Z) |
| His | N—tosyl |
| Ser | O—benzyl ether |

-continued

| Amino Acid | Protecting Group |
|---|---|
| Arg | N—tosyl |
| Tyr | O—benzyl ether. |

Coupling of each amino acid was carried out using dicyclohexylcarbodiimide coupling agent in each case. With the amino acids Arg, Asn, Gln, Phe, and Ser, a molar equivalent of hydroxybenzotriazole was used with the dicyclohexylcarbodiimide.

The blocked peptide was removed from the resin by reaction with hydrogen fluoride in the presence of anisole at 0° for 1 hour. The peptide was purified by ion exchange chromatography using ammonium acetate, followed by gel filtration using 30% aqueous acetic acid and then 50% aqueous acetic acid for elution.

Peptide 1b was soluble in water at 25°, and in 1:1 acetonitrile/water and 1:1 dimethyl sulfoxide/water. The infrared spectrum (Nujol mull) exhibited the broad NH peak (3300 cm$^{-1}$) and carbonyl peaks (1650–1670 cm$^{-1}$) typical of non-crystalline peptides. There was no evidence of nitrile absorption (2200 cm$^{-1}$) which showed that dehydration of glutamine and asparagine amide groups had not occurred to a significant extent. High pressure liquid chromatography on a Du Pont Zorbax C8 L-1109 reverse phase column using UV detection at 210, 254, 275, and 350 nm, and nmr spectrum (220 MHz; D$_2$O solvent) indicated that the product contained a large quantity of impurities. Presence of impurities was verified by micro automated Edman degradation on a spinning cup sequenator, described by Hunkapiller and Hood, Science 207, 523 (1980). The results together indicate that the peptide contains no more than about 0.3% of unblocked peptide 1b.

PREPARATION C

Preparation Of Peptide Sequence 1c (Wherein X is Met and Y is Cys)

Peptide 1c can be made by the general procedure described in Preparation A for making Peptide 1a with the exception that cysteine is used in place of histidine in the Y position.

PREPARATION D

Preparation of Peptide Sequence 1d (Wherein X is Ser and Y is Cys)

Peptide 1d can be made by the general procedure described in Preparation A for making Peptide 1a with the exception that serine is used in place of methionine in the X position and cysteine is used in place of histidine in the Y position.

The amino acid sequences of Peptides 1a, 1b, 1c, and 1d can be verified by the routine, extended N-terminal sequence analysis described by Hunkapiller et al in Biochemistry, Vol. 17, No. 11, 1978, pages 2124 to 2133; and Bell et al in Proc. Natl. Acad. Sci. USA, Vol. 75, No. 6, 1978, pages 2722 to 2726.

PREPARATION E

Oligomerization of Peptide Sequence 1b (n=2–12)

Water used in this Example was deionized water distilled in a glass apparatus. When deaerated water was used, it was deaerated by successive nitrogen purges followed by the application of vacuum.

To a solution of 40.0 mg of peptide sequence 1b, prepared as described in Preparation B, in 10 ml of water, was added 10 μl of $^{125}$I-labeled peptide sequence 1b with stirring. Two separate 50 μl aliquots were withdrawn for counting. The solution was cooled in ice and a solution of 600 mg of N-ethyl-5-phenylisoxazolium-3'-sulfonate (NEPIS; Woodward's Reagent K) in 4.0 ml of water was added. The pH of the resulting solution was 3.9, and the solution had a faint yellow color. The solution was stirred at 0° to 5° while a 2.00 N solution of sodium hydroxide in water was added dropwise. The pH rose and fell back with each addition. When 1.20 ml had been added, the pH was 7.8 and remained steady. The resulting solution was stirred in ice for 1 hr and two 50 μl aliquots were withdrawn for counting for radioactive iodine (99% of the original count was retained).

The reaction mixture was transferred to a 50 ml centrifuge tube, and it was centrifuged at 8000 rpm for 20 min. The supernatant, after removal of two 50-μl aliquots for counting (45% of original count), was withdrawn and stored at −80°.

The adherent gray pellet was resuspended in 15 ml of water and triturated with a glass rod followed by strong mechanical agitation to resuspend it. The suspension (after withdrawal of two 50 μl samples for counting; 47% of original count) was centrifuged for 20 min at 8000 rpm. The resulting supernatant contained 21.5% of the original counts.

The resulting pellet was resuspended in 15 ml of water, and two 50 μl aliquots were withdrawn for counting; 31.5% of original count. The suspension was centrifuged for 10 min at 8000 rpm, and two 50 μl aliquots of the supernatant were withdrawn for counting; 5.2% of original count. The supernatant was then withdrawn and the pellet was dissolved in 0.5 ml of dimethyl sulfoxide to form a yellow solution. The solution was added with stirring to sufficient isotonic sodium chloride solution to give 10.5 ml of a cloudy aqueous suspension. A 100-μl aliquot was removed for counting, and 32% of the original count was retained.

These results show that 30.6% (12.3 mg) of the initial peptide sequence was incorporated into the water-insoluble peptide oligomer.

EXAMPLE 1

Covalent Attachment (Conjugation) of Peptide Sequence 1b to Ovalbumin

The procedure involved the attachment of an iodoacetyl group to the lysine side-chain of the peptide, and thiol groups to the lysine side-chains of ovalbumin. Subsequent reaction of the two modified components resulted in formation of a covalent thioether bond. Little or no reaction of either the modified peptide or modified ovalbumin with itself occurs in a nitrogen atmosphere.

A. Iodacetylation of Peptide Sequence 1b

To a solution of 40.0 mg of peptide sequence 1b, prepared as described in Preparation B, in 6.0 ml of deionized and deaerated water (pH=5.8) was added 12 μl of $^{125}$I-labeled peptide sequence 1b with stirring. A 50 μl aliquot was withdrawn for counting. Fifty μl of aqueous 1 M sodium bicarbonate solution was added slowly to bring the pH to 6.9. The solution was stirred at 25° and 150 μl of a freshly prepared solution of iodoacetic acid N-hydroxysuccinimide ester, prepared by dissolving 28 mg of iodoacetic acid N-hydroxysuccinimide ester in 0.70 ml of dioxane, was added slowly. The pH dropped to 6.4. About 100 μl of additional sodium bicarbonate solution was added slowly to bring the pH to 7.0. After 15 min a 50 μl aliquot was withdrawn for counting; 89% of original count.

The solution was held at 5° overnight. The reaction product was warmed to room temperature and 40 μl of glacial acetic acid was added; pH=4. The mixture (6.2 ml) was centrifuged at room temperature. The pellet was triturated with 1 ml of 0.1 M acetate buffer having a pH of 4.5, and recentrifuged. The combined supernatants (7.2 ml) were recentrifuged at 8000 rpm. A 1 ml aliquot of the supernatant was removed for counting; 65% of original count.

The supernatants and 100 mg of dinitrophenylalanine were placed on a 1.6×100 cm G-25 Sephadex column and eluted with 0.1 M, pH 4.5, acetate buffer. A total of 79 fractions of 3.7 ml each were collected and counted. The major peak of radioactivity occurred with fractions 26, 27, and 28. These were combined (11.0 ml total). The dinitrophenylalanine peak eluted at fraction 74. The pooled fractions 26 to 28 were centrifuged at 3000 rpm in two Oak Ridge tubes. An aliquot of the supernatant (10.5 ml) was counted; 16.5% of original count. It was divided into two equal portions for reaction with ovalbumin.

B. Thiolation of Ovalbumin

Ovalbumin, 64.0 mg, twice recrystallized, was added slowly at 0° to 5.0 ml of pH 8.55 borate buffer (0.1 m) and stirred gently for a few minutes. The solution was allowed to stand about 1 hr and it was then stirred gently and freed of air by successive purges with nitrogen and application of vacuum. Then, 194 mg of iminothiolane hydrochloride was added under nitrogen. The solution was allowed to warm to room temperature and was stirred gently for 1 hr under nitrogen. The solution was transferred under nitrogen to a dialysis bag and dialyzed overnight against 1000 ml of phosphate buffered saline (1:10) at pH 7.2. The buffer had been freed of oxygen by nitrogen and vacuum purging as above. During the dialysis, agitation was achieved by using a nitrogen bubbler. The dialysate was then further dialyzed against 1000 ml of deaerated distilled water for 4 hrs. The resulting solution was divided into two equal 2.5 ml portions and stored briefly under nitrogen pending reaction with the iodoacetylated peptide of Part A.

C. Preparation of Protein/Peptide Conjugate

A 2.5 ml portion of thiolated ovalbumin solution of Part B was placed under nitrogen in a 20 ml sample vial and cooled to 0°. A solution of 5.0 ml of iodoacetylated peptide of Part A was added dropwise under nitrogen. There was no noticeable precipitation although after 2 hrs at 5° a faint cloudiness was detected. The pH of the solution was 4.5. A 200 μl portion was removed for counting. The reaction mixture was purified by dialysis against 0.1 M acetate buffer having a pH of 4.5. The retentate was redialyzed against 0.01 M borate buffer, pH 8.55. Most of the precipitate redissolved. The retentate was then centrifuged at 500×g for 20 min and the supernatant was used in subsequent immunological studies.

In a second preparation the order of addition was reversed. A 5.0 ml portion of the iodoacetylated peptide of Part A was placed in a 125 ml Erlenmeyer flask under nitrogen and 2.5 ml of thiolated albumin solution of Part B was added dropwise at 0°. There was no visible precipitation. A 200 μl portion was removed for counting. The remaining 7.3 ml of solution was allowed to stand for 3 days at 5° and was the dialyzed against distilled water and against borate buffer at pH 8.55. The retentate was centrifuged as above. Immunological studies showed the two preparations were essentially equivalent.

EXAMPLE 2

Conjugation of Peptide Sequence 1a to Rabbit Albumin

A solution of 30 mg of rabbit albumin in 3 ml of 0.01 M 2-(4-morpholino)ethanesulfonic acid (MES) buffer at pH 4.5 was stirred at 0° in a 50 ml flask for 1 hr. A solution of 20 mg of the peptide sequence 1a in 1.0 ml of water was treated with 200 μl of a solution of the peptide labeled with $^{125}$I.

The peptide solution was added to the stirred albumin solution and then a solution of 80 mg of N-ethyl-5-phenylisoxazolium-3'-sulfonate in 2.0 ml of water was added. Aqueous sodium hydroxide (2 N) was added to maintain the pH at 5.0 to 5.8. After stirring 30 minutes at 0° the reaction mixture was dialyzed for 24 hrs against 1 liter of 0.008 M borate buffer, pH 8.5. The dialysis was repeated against fresh buffer. The retentate was then centrifuged as above. The resulting supernatant was recentrifuged and the final supernatant was retained for immunological studies. An aliquot was withdrawn for counting; it showed that this supernatant contained 8.5% of the original count.

The pellet from the first centrifugation was washed with 8 ml of borate buffer and the mixture recentrifuged. The supernatant was again centrifuged and this second supernatant was retained for immunological studies. An aliquot was removed for counting; 4% of original count. Reprocessing of the pellet with borate buffer and centrifugation as described gave a third supernatant; 4% of original count.

EXAMPLE 3

Conjugation of Peptide Sequence 1a to Ovalbumin

A solution of 45 mg of ovalbumin in 4.5 ml of 0.01 M MES buffer (pH 4.1) was treated at 0° with a solution of 30 mg of the peptide of sequence 1a in 1.50 ml of water and 300 μl of the $^{125}$I-labeled peptide of sequence 1a. To this solution was added a solution of 120 mg of N-ethyl-5-phenylisoxazolium-3'-sulfonate in 3.0 ml of water, and the reaction mixture was stirred. The pH dropped to 4.9. Sodium hydroxide solution (2 N) was added to keep the pH at 5.5 to 6, and the solution was stirred for 30 minutes at 0°. The milky white reaction product was transferred to a dialysis bag and dialyzed at 5° twice against 0.01 M borate buffer (16 hrs; then 5 days). The retentate was centrifuged and the supernatant was dialyzed against 0.01 M borate buffer for 3 days at 5°. The retentate was centrifuged and the supernatant conjugate was retained for use in immunological studies. An aliquot was withdrawn for counting; it showed that this supernatant contained 41% of the original count.

The initial pellet was successively washed with 0.01 M borate and recentrifuged three times to give a final washed pellet which was retained for use as an immunogen in immunological studies.

EXAMPLE 4

Conjugation of Peptide Sequence 1a to Ovalbumin

The procedure used was substantially as that employed for the conjugation of peptide sequence 1b (Example 1).

A. Iodoacetylation of Peptide Sequence 1a

A solution of 20 mg (about 10 μmoles) of peptide sequence 1a in 3 ml of deaerated distilled water was spiked with about 12 μg of $^{125}$I-labeled peptide and an aliquot was removed for counting. The pH was adjusted to 8.5 with 0.01 N sodium hydroxide solution. A total of 75 μl of a solution of iodoacetic acid N-hydroxysuccinimide ester in dioxane (28 mg/700 μl dioxane) was added. The reaction mixture became opaque, milky white and the pH dropped to 6.8. Sodium hydroxide solution (0.01 N) was added slowly to increase the pH to 8. The reaction mixture was stirred for 30 minutes. The mixture was centrifuged and the pellet was separated and recentrifuged. The pellet was dissolved in 0.80 ml of dimethyl sulfoxide.

B. Thiolation of Ovalbumin

A solution of 32.0 mg of ovalbumin in 2.5 ml of 0.1 M borate buffer, pH 8.55, was stirred at 0° in an ice bath and freed of oxygen by successive vacuum purges alternating with the admission of nitrogen. The resulting oxygen-free solution was treated with 97 mg of iminothiolane hydrochloride, and the reaction mixture was allowed to warm to room temperature. It was stirred gently under nitrogen for 2 hrs. The reaction mixture was subjected to dialysis against 1000 ml of deaerated, distilled water using a nitrogen bubbler for agitation. The product volume was 2 ml.

C. Preparation of Protein/Peptide Conjugate

The thiolated ovalbumin solution of Part B was placed in a 25 ml flask under nitrogen; a total of 8 mg of solid sodium bicarbonate and 3 mg of sodium carbonate were added with stirring. The pH was 9.0. The dimethyl sulfoxide solution of iodoacetylated peptide from Part A was added dropwise under nitrogen over a period of 5 minutes and the pH rose to 9.8. To destroy unreacted thiol groups, 100 mg of iodoacetamide was added and the resulting solution was stirred for 5 minutes. The reaction mixture containing the protein conjugate was centrifuged for 10 minutes at 8000 rpm, and the supernatant was removed.

The pellet was suspended in distilled water and dialyzed against 0.01 M borate buffer at pH 8.1 for 15 hrs, then against fresh borate buffer for 6 hrs. The resulting solid product was retained for use in immunological studies. The supernatant (4.0 ml) was separately dialyzed against borate buffer as described, and it was stored for use as an immunogen in immunological studies.

EXAMPLE 5

Test For Antibodies In Sera From Mice And Rabbits Injected With Synthetic Peptide 1b In order to detect antibodies from the injected animals a solid phase radioimmune assay was used. In the first step a borate buffer (0.01 M, pH 8.55) solution of the peptide-protein conjugate of Example 1 was placed in each well of a polyvinyl microtiter plate well in order to allow the peptide conjugate to adhere to the plastic.

Typically, the peptide-ovalbumin conjugate contained 180 micrograms of peptide per milliliter as measured by incorporation of a $^{125}$I-radiotracer peptide. The one hundred microliter volume was allowed to incubate overnight at 4°. The microtiter wells were emptied and washed three times with Dulbeccos' phosphate buffered saline solution (pH 7.2) containing 1 mg per milliliter of bovine serum albumin and 0.02% sodium azide. In some experiments the bovine serum albumin was replaced by coating with the plant protein ribulose biphosphate carboxylase for 10 minutes at 37°.

In the next step, one hundred microliters of various dilutions of serum from the various immunized animals was placed in each well and allowed to incubate for one hour at 37°. After aspirating the serum dilutions from the well, the wells were washed three times with phosphate buffered saline solution (pH 7.2), and one hundred microliters of radioiodinated ($^{125}$I) commercially available Protein A was added per well. This solution contained approximately 20 ng of Protein A per milliliter (approx. specific activity 1 $\mu$Ci per microgram). The Protein A solution was allowed to incubate at least 1 hr at 37° and then aspirated out of the wells. The wells were washed three times with phosphate buffered saline, pH 7.2, dried, cut with a hot wire cutter and counted in a Packard gamma counter. The amount of radioactive Protein A bound was related to the antibody titer of the serum.

The radioimmune assay procedure was a slight modification of the published procedure of Marier et al., J. Immunol. Methods, 28, 41 to 49 (1979), which is reportedly able to detect as little as one nanogram of antibody per milliliter. Thus, the hyperimmune serum was estimated to contain at least one to one hundred micrograms of specific antibody per milliliter.

EXAMPLE 6

Test For Ability Of Mouse and Rabbit Antibody To Synthetic Peptide 1a To React With Radioiodinated Human Fibroblast Interferon Using A Solid Phase Reagent Serum samples from ice and rabbits immunized with peptide 1a were diluted ten-fold with a sodium phosphate buffered saline solution (pH 7.2) containing 0.1% w/v bovine serum albumin and 0.02% of sodium azide (Buffer A). Serum samples from non-immunized mice and rabbits as well as a goat anti-interferon serum Control prepared by conventional methods were diluted in a similar manner.

To ten microliter portions of these sera was added ten microliters of radioiodinated ($^{125}$I) human fibroblast interferon (approximately 2,400 cpm specific activity, approximately 20 $\mu$Ci per microgram.) After 30 minute incubation of the samples in a humidified 37° incubator, 300 microliter amounts of formalin-killed *Staphylococcus aureus* was added to each sample and they were re-incubated for an additional 20 minutes at 37°. A 0.7 ml volume of Buffer A was added to each tube, the tubes were agitated in a vortex mixer and centrifuged in an Eppendorf centrifuge. The supernatant solutions were removed with a Pasteur pipet and the sediments resuspended in one milliliter of Buffer A. The tubes were twice recentrifuged as described, each time using 1 ml of Buffer A and resuspending the sediment. The washed sediment was finally resuspended in one ml of Buffer A, transferred to a clean centrifuge tube, and placed in a gamma counter to determine the sedimented radioiodine.

The results demonstrated that rabbits and C$_3$H mice immunized with synthetic peptide 1a bound radioactive labeled human fibroblast interferon. The C$_3$H mouse sera bound approximately 0.03 ng per 10 microliters of a one to ten dilution while the goat anti-interferon Control bound 0.06 ng at the same dilution.

EXAMPLE 7

Assay For Human Fibroblast Interferon Using Antibody to Synthetic Peptide: A Double Antibody Assay Four microliters of radioiodinated ($^{125}$I) interferon (5,600 cpm, specific activity of a about 10 $\mu$Ci per $\mu$g) was added to polycarbonate centrifuge tubes containing ten microliter volumes of either immune sera (C$_3$H mice, rabbit, and goat antiinterferon Control) or normal mouse and rabbit sera. The tubes were incubated for 1½ hours at 37° and then forty microliters of rabbit anti-mouse IgG (immunoglobulin G) was added to each tube containing mouse serum, sixty microliters of an IgG fraction of goat anti-rabbit IgG to the tubes containing rabbit serum, and one hundred microliters of rabbit antigoat IgG to the tube containing goat serum. All tubes were incubated for 1½ hrs at 37° and then centrifuged in a Fisher centrifuge for 5 minutes at 5,000×g.

The supernatants were removed by Pasteur pipet and the radioactivity of the sediments and supernatants was measured in a Packard gamma counter. The radioactive pellets were resuspended in a solubilizing solution containing 0.01 M tris (hydroxymethyl)aminomethane hydrochloride (Tris) buffer, pH 6.8, 1% w/w sodium dodecyl sulfate, 10% glycerol, and 0.02 m thioglycolic acid. The solutions were placed in boiling water for 1 minute and then applied to separate tracks on a slab gel containing a gradient of 10% to 16% acrylamide. After electrophoresis for 5 hrs the gel was removed, fixed (10% acetic acid), and stained with Coomassie blue. Autoradiograms of the gel were prepared by exposing film for first one week, then four weeks.

This experiment demonstrated that a pool of serum for C$_3$H mice immunized with synthetic peptide 1a and a rabbit immunized with the same peptide both reacted with radioactive native human fibroblast interferon and that the radioiodine precipitated subsequently migrated on gel electrophoresis with the same mobility as native fibroblast interferon.

EXAMPLE 8

Anti-Peptide 1a Rabbit Antibody Used to Purify Human Fibroblast Interferon In An Affinity Column Serum from a rabbit immunized with synthetic peptide 1a was diluted with 0.66 volume of phosphate buffered saline (PBS), and immunoglobulins were precipitated by gradual addition of saturated ammonium sulfate (1.36 volume). Precipitated immunoglobulins were redissolved in PBS and reprecipitated by the same procedure. The twice precipitated antibodies were then dissolved in 0.1 M borate buffer, pH 8.5, and dialyzed against the same buffer. Insoluble impurities were removed by centrifugation (10 min, 10,000×g).

The soluble rabbit antibodies were immobilized by coupling to agarose beads ("Sepharose 4B", Pharmacia) by modification of standard procedures using cyanogen bromide as discussed by Parikh et al. in "Affinity Chromatography In Immunology" in "Immunochemistry of Proteins", Vol. 2, edited by M. Z. Atassi, Plenum Press, New York, 1979, pages 1 to 44. Agarose beads (40 ml) were washed and suspended in water (75 ml total volume), and a solution of 4 g of cyanogen bromide dissolved in 5 ml of acetonitrile was added. The mixture was mechanically stirred while 4 M sodium hydroxide was added to maintain the pH at 11.0. When the reaction was ended (approximately 25 min), the beads were washed on a filter funnel with ice-cold borate buffer. Packed and drained beads (10 gm) were added to 18 ml of borate buffer containing approximately 40 mg of soluble rabbit antibodies, and the mixture was kept in suspension for 72 hrs at 4°. The supernatant fluid was removed by centrifugation (600×g, 15 minutes).

Approximately 93% of the total proteins were adsorbed on the beads as shown by light absorption at 280 nm. The packed beads were resuspended for 18 hrs at 4° in 18 ml of 0.1 M glycine, pH 9.5, in order to "block" unreacted sites. The beads were then loaded into a 1.5×10 cm column and washed with 40 ml each of: PBS; 0.5 M sodium chloride, 0.05 M sodium phosphate, pH 6.4; and 0.05 M sodium phosphate, pH 6.4, containing 0.5% Tween-80. Then, the beads were washed 36 hrs (5 ml/hr) with PBS.

Washed, packed beads (5 g) were mixed with 10 ml of a preparation of crude interferon (320 units) containing $^{35}$S-labeled cellular proteins. The mixture was kept in suspension for 3 hrs to permit adsorption of interferon. The beads were sedimented, washed with PBS by low speed centrifugation and then loaded onto a 1.5 cm diameter column. The column was washed at a flow rate of approximately 8 ml/hr with 16 ml of PBS, 13 ml of 0.15 M sodium acetate buffer (pH 4.5), and 14 ml of 0.1 M glycine (pH 2.5). Fractions of approximately 2 ml were collected. Biologically active interferon (242 units) and 0.1% of the total $^{35}$S was eluted in a volume of 9 ml just ahead of the pH 2.5 glycine buffer.

These results demonstrated that rabbit antibody to synthetic peptide 1a was useful in the purification of human fibroblast interferon resulting in an approximate purification factor of 1000 and yielding over 50% recovery of the biologically active interferon.

The embodiments of the invention in which an exclusive property or privilege is claimed are defined as follows:

1. A process for purifying human fibroblast interferon contained in a liquid phase mixture of proteins, comprising (i) contacting the protein mixture with antibodies produced in response to the peptide having the amino acid sequence:

(X-Ser-Tyr-Asn-Leu-Leu-Gly-Phe-Leu-Gln-Arg-Ser-Ser-Asn-Phe-Gln-Y-Gln-Lys-Leu-Leu)$_n$ wherein:
X is selected from Met and Ser,
Y is selected from His and Cys, and
n is 1 to 12;
and forming an interferon-antibody complex; (ii) separating the interferon-antibody complex from the liquid phase; and (iii) separating the interferon from the antibody.

2. A process for purifying protein and protein fragments of human fibroblast interferon contained in a liquid phase mixture of proteins, said protein and protein fragments containing one or more of the peptide sequences defined in step (i) the process comprising (i) contacting the protein mixture with antibodies produced in response to the peptide having the amino acid sequence:

(X-Ser-Tyr-Asn-Leu-Leu-Gly-Phe-Leu-Gln-Arg-Ser-Ser-Asn-Phe-Gln-Y-Gln-Lys-Leu-Leu)$_n$ wherein:
X is selected from Met and Ser,
Y is selected from His and Cys, and
n is 1 to 12;
and forming a complex of the antibody with the protein or protein fragment of human fibroblast interferon; (ii) separating the complex from the liquid phase; and (iii) separating the protein and protein fragments of the interferon from the antibody.

* * * * *